United States Patent [19]

Frankel et al.

[11] 4,419,285

[45] Dec. 6, 1983

[54] AZIDO FLUORODINITRO AMINES

[75] Inventors: Milton B. Frankel, Tarzana; Edward F. Witucki, Van Nuys, both of Calif.

[73] Assignee: The United States of America as represented by the Secretary of the Air Force, Washington, D.C.

[21] Appl. No.: 350,494

[22] Filed: Feb. 19, 1982

[51] Int. Cl.$^3$ ............................................. C07C 117/00
[52] U.S. Cl. ....................................... 260/349; 149/88; 149/19.1; 149/19.3; 149/19.5
[58] Field of Search .............. 260/349; 149/19.1, 19.3, 149/19.5, 88

[56] References Cited

U.S. PATENT DOCUMENTS

| | | | |
|---|---|---|---|
| 3,122,570 | 2/1964 | Stansbury et al. | 260/349 |
| 3,356,714 | 12/1967 | Kamlet | 149/88 X |
| 3,564,055 | 2/1971 | Zimmerman | 260/584 |
| 3,576,840 | 4/1971 | Frankel | 149/88 X |
| 3,629,324 | 12/1971 | Frankel et al. | 149/88 X |
| 3,629,338 | 12/1971 | Martin | 149/19.3 X |
| 3,645,917 | 2/1972 | Vandenberg | 260/2 A |
| 3,705,197 | 12/1972 | Kaplan et al. | 260/615 A |
| 3,784,420 | 1/1974 | Frankel et al. | 149/88 X |
| 3,832,390 | 8/1974 | Frankel et al. | 149/19.3 X |
| 3,873,579 | 3/1975 | Rosher | 260/349 |
| 3,873,617 | 3/1975 | Adolph et al. | 149/92 X |
| 3,922,311 | 11/1975 | Peters et al. | 260/615 A |
| 4,020,176 | 4/1977 | Greenwald | 260/349 |
| 4,141,910 | 2/1979 | Flanagan et al. | 149/88 X |

OTHER PUBLICATIONS

Boyer et al., Chemical Reviews, 54, (1954), p. 48.

Primary Examiner—Joseph Paul Brust
Attorney, Agent, or Firm—Donald J. Singer; William J. O'Brien

[57] ABSTRACT

This invention involves the synthesis of a novel family of azido fluorodinitro amines and their utilization as energetic plasticizers for advanced solid propellant compositions.

2 Claims, No Drawings

AZIDO FLUORODINITRO AMINES

STATEMENT OF GOVERNMENT INTEREST

The invention described herein may be manufactured and used by or for the Government for governmental purposes without the payment of any royalty thereon.

BACKGROUND OF THE INVENTION

This invention relates to solid propellant compositions and to a novel family of plasticizers for use therewith. In a more specific aspect, this invention concerns itself with the use of a novel family of azido fluorodinitro amines as energetic plasticizers for advanced solid propellant compositions. In still another specific aspect, this invention concerns itself with the use of azido fluorodinitro amines as a means of reducing or minimizing the amount of smoke in the exhaust gases generated during the propulsion phase of solid propellants.

The increased utilization of rockets and missiles has spawned a considerable research effort in an attempt to improve the performance characteristics of solid propellant compositions. Generally, solid propellants consist of one or more organic or inorganic oxidizers dispersed in a resinous binder matrix which may also function as a fuel. Typical oxidizers are ammonium perchlorate or HMX (cyclotetramethylene tetranitramine) which are well known in the art. Various resinous components, such as hydrocarbons, polyesters, polyurethanes and other like materials serve as the binder/fuel matrix. A supplemental fuel component such as finely powered aluminum, may be used also. Other additive components, such as anti-oxidants, burning rate modifiers, wetting agents, anti-foaming agents and plasticizers may be added to the propellant composition, if desired. Dibutylphthalate or triacetin are generally employed as inert plasticizers in combination with the resinous binder material.

In using solid propellants, however, a problem exists in that an undesirable amount of smoke is often produced in the exhaust gases emanating from the solid rocket motor during propulsion. Excessive amounts of smoke are extremely undesirable in the exhaust gases since this provides data which pinpoints the sites from which the missiles or rockets are being fired. During previous efforts at overcoming the problem of excessive smoke, it was suggested that HMX be utilized as the oxidizer component since ammonium perchlorate liberates hydrochloric acid as a primary exhaust product. The acid is a strong smoke producer. Although the use of HMX as an oxidizer tended to reduce the amount of smoke produced in the exhaust gases, its use did not sufficiently overcome the problem and telltale amounts or smoke were still produced.

As a consequence, a continuing research effort was maintained since there still existed a need for a solid propellant with a minimum amount of smoke in the exhaust gases coupled with performance characteristics as good or better than solid propellants that have excessive amounts of smoke in their exhaust gases. In furthering the research effort referred to above, it was unexpectedly discovered that a new family of azido fluorodinitro amines could be employed as energetic plasticizers in the fabrication of an energetic, smokeless propellant. The novel plasticizers of this invention replace the conventional inert plasticizer utilized in a conventional HMX composite propellant and the resulting propellant not only produces a minimum amount of smoke during propulsion but, also, shows a significant improvement in specific impulse characteristics.

SUMMARY OF THE INVENTION

In accordance with this invention, there is provided a novel family of azido fluorodinitro amines which are energetic liquids and find particular utility as energetic plasticizers in advance solid propellants. Azidomethyl bis(flurodinitroethyl) amine (AMFA) and 0-(1,2-diazidopropyl) N,N-bis(fluorodinotroethyl) amino methanol (DAFAM) are two examples of this family of amines which have been found to be unexpectedly effective in overcoming the problem of smoke in the exhaust gases produced during the operational phase of a solid propellant composition. The energetic plasticizers of this invention replace the conventional inert plasticizers and are used in the propellant in a ratio of from about 1.5 to 4.0 parts of plasticizer to about 1.0 part of binder to produce a significant increase in energy coupled with a minimum production of smoke.

Accordingly, the primary object of this invention is to provide a novel family of azidofluorodinitro amines.

Another object of this invention is to provide a novel solid propellant composition that produces only minimum amounts of smoke during propulsion.

Still another object of this invention is to provide a novel family of azido fluorodinitro amines that find particular utility as energetic plasticizers for advanced solid proepllant compositions.

The above and still other objects and advantages of the present invention will become more readily apparent upon consideration of the following detailed description thereof.

DESCRIPTION OF THE PREFERRED EMBODIMENTS

With the above-mentioned and other objects in mind, the present invention contemplates the synthesis of a novel family of azido fluorodinitro amines and their utilization as energetic plasticizers in a conventional HMX containing solid composite propellant. This novel family of amines includes azidomethyl bis(flurodinitroethyl) amine (AMFA) and 0-(1,2-diazidopropyl)N,N-bis(fluorodinotroethyl) amino methanol (DAFAM). Both AMFA and DAFAM possess physicalproperties that make them suitable for plasticizer use and are considerably more attractive than a conventional plasticizer such as (2,2,2-fluorodinitroethyl) formal (FEFO). Compared to FEFO, the AMFA has higher energy (−33 versus −178 kcal/mole), higher density (1.638 versus 1.596), lower freezing point (−5 to 0 C versus ±14 C), and lower weight loss for 72 hours at 165 F (2.4 versus 10.6%). Compared to FEFO, the DAFAM has higher energy (+8 versus −178 kcal/mole), lower freezing point (5 to 10 C versus 14 C) and lower weight loss for 72 hours at 165 F (3.1 versus 12.4%).

The synthesis of azidomethyl bis(fluorodinitroethyl) amine (AMFA) was accomplished by the reaction of bromomethyl bis(fluorodinitroethyl) amine and sodium azide as shown by the following equation:

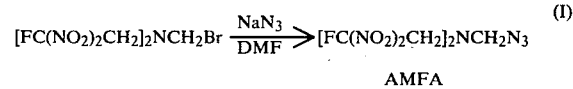

(I)

AMFA

Example 1 discloses the experimental details of the reaction illustrated by equation (I).

EXAMPLE 1

A solution of 30 g (0.079 moles) of bromomethyl bis(fluorodinitroethyl) amine in 80 ml of DMF, under a nitrogen blanket, was cooled to 0° C. Sodium azide (10.2 g; 0.157 moles) was added at 0° C. and the reaction mixture was then stirred at this temperature overnight. Gas chromatographic analysis at this point showed the disappearance of starting material and the appearance of one new material. Reaction solids were removed by centrifugation, an equal quantity of methylene chloride was added, and the organic mixture was washed ten times with water to remove DMF. Removal of methylene chloride yielded 24.2 g (90% yield) of crude AMFA. Pure AMFA was isolated as colorless liquid by means of liquid chromatography using silica gel as the adsorbent.

| Elemental Analyses | C | H | N |
|---|---|---|---|
| Calculated for $C_5H_6F_2N_8O_8$ (%): | 17.45 | 1.76 | 32.56 |
| Found (%): | 17.52 | 2.92 | 32.67 |

The infrared spectrum showed the characteristic absorption for azide (4.8u) and fluorodinitro (6.3u).

The synthesis of 0-(1,2-Diazidopropyl)N,N-bis(-fluorodinitroethyl) amino methanol (DAFAM) was accomplished by the condensation reaction of bromomethyl bis(fluorodinitroethyl) amine and 2,3-diazido-1-propanol as illustrated by the following equation:

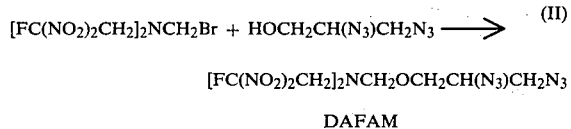

$$[FC(NO_2)_2CH_2]_2NCH_2Br + HOCH_2CH(N_3)CH_2N_3 \longrightarrow \quad (II)$$

$$[FC(NO_2)_2CH_2]_2NCH_2OCH_2CH(N_3)CH_2N_3$$

DAFAM

The experimental details of the reaction of equation (II) are shown in Example 2.

EXAMPLE 2

A solution of 11.8 g (0.031 moles) of bromomethyl bis(fluorodinitroethyl) amine in 75 ml of acetonitrile, under a nitrogen blanket, was cooled to 0° C. To this cold solution was added 4.38 g (0.031 moles) of 2,3-diazido-1-propanol followed by the dropwise addition of 3.12 g (0.031 moles) of triethylamine. The reaction mixture was stirred at 0° C. for one hour, then at ambient temperature overnight and finally at 50° C. for four days. Periodic ir and gc analysis dictated the reactions length and also its temperature. At reactions end there remained a heavy slurry of white solid. Acetonitrile was removed and to the resulting solids-oil mixture was added 100 ml of ether. In this way, the oil was completely solubilized and the solid remained insoluble. The solid was filtered and identified as triethylamine hydrobromide. The filtrate was concentrated yielding 13 g of yellow oil. Pure DAFAM was isolated from this yellow oil in about 50% yield via liquid chromatography using silica gel as the adsorbent.

| Elemental Analysis | C | H | N |
|---|---|---|---|
| Calculated for $C_8H_{11}O_9N_{11}F_2$ (%): | 21.68 | 2.50 | 34.76 |
| Found (%): | 21.56 | 2.57 | 35.34 |

The infrared spectrum showed the characteristic absorption for azide (4.8μ) and fluorodinitroethyl (6.3μ).

The properties of AMFA and DAFAM are summarized, respectively, in Tables I and II as follows:

TABLE I
PROPERTIES OF AMFA

| NAME: | Azidomethyl bis(Fluorodinitroethyl) amine | |
|---|---|---|
| CODE: | AMFA | |
| STRUCTURE: | $[FC(NO_2)_2CH_2]_2NCH_2N_3$ | |
| FORMULA: | $C_5H_6F_2N_8O_8$ | |
| MOLECULAR WEIGHT: | 344 | |
| FREEZING POINT (C): | Glasses at −5 to 0 | (FEFO = +14) |
| DENSITY (g/cc at 23 C): | 1.638 | (FEFO = 1.596) |
| REFRACTIVE INDEX (23.5 C): | 1.4865 | |
| IMPACT SENSITIVITY (in-lb): | 13 | (FEFO = 90) (SYEP = 5) |
| WEIGHT LOSS AT 165 F (%): | | |

| | 24 hrs | 48 hrs | 72 hrs | 96 hrs |
|---|---|---|---|---|
| AMFA: | 1.0 | 1.2 | 2.4 | 2.9 |
| FEFO: | 3.8 | 6.8 | 10.6 | 13.1 |

ΔH$_f$(kcal/mole): −33   (FEFO = −178)

TABLE II
PROPERTIES OF DAFAM

| NAME: | [0(1,2-Diazidopropyl)N,N—bis(Fluorodinitroethyl)] Amino Methanol |
|---|---|
| CODE: | DAFAM |
| STRUCTURE: | $[FC(NO_2)_2CH_2]_2NCH_2OCH_2CH(N_3)CH_2N_3$ |
| FORMULA: | $C_8H_{11}O_9N_{11}F_2$ |
| MOLECULAR WEIGHT: | 443 |
| FREEZING POINT (C): (FEFO = 14) | Glasses at 5-10 |
| DENSITY (g/cc at 23 C): | 1.521 |
| REFRACTIVE INDEX (23 C): | 1.4932 |
| WEIGHT LOSS FOR 72 HRS at 165 F (%) | DAFAM 3.1 FEFO 12.4 |
| ΔH$_f$(kcal/Mole): | +8   (FEFO = −178) |

The unexpected benefits achieved by replacing the inert plasticizer commonly employed in HMX/polyester based solid propellants with the novel energetic liquid plasticizers of this invention is further illustrated in Table III. Although an HMX oxidizer and a polyester resin binder are preferred, other conventional oxidizing and resinous binders may be utilized, if desired, as well as other fuel components, such as powdered aluminum.

Solid propellant compositions are well known and since the basic preparation and constituent ingredients of the propellant compositions of this invention are not significantly altered or critical to the execution of the invention, with the exception of the energetic plasticizer component, a detailed explanation of the propellants preparation is not deemed necessary. The plasticizers of this invention are liquid in nature and are incorporated into the solid propellant mix in a conventional manner at any stage of processing prior to cure. The resulting solid propellant differs from a conventional composition only in the essential replacement of the typical inert plasticizer with the novel energetic plasticizers of this invention.

TABLE III

EFFECT OF SUBSTITUTING AMFA AND DAFAM FOR TRIACETIN (TA) IN A HMX SMOKELESS PROPELLANT

| Propellant Composition (Weight %) | | | |
|---|---|---|---|
| HMX | 75 | 75 | 75 |
| Polyester resin | 10 | 10 | 10 |
| TA | 15 | — | — |
| AMFA | — | 15 | — |
| DAFAM | — | — | 15 |
| Theoretical Performance ($P_c$ = 1000 14.7 psi) | | | |
| $I_{sp}$ | 211 | 245 | 242 |

TABLE III-continued

EFFECT OF SUBSTITUTING AMFA AND DAFAM FOR TRIACETIN (TA) IN A HMX SMOKELESS PROPELLANT
(lb-sec/lb)

Of particular interest in the above propellants is the fact that the specific impulse increase, which is effected by such a substitution is 31-35 Lbf-sec/Lbm-a significant improvement. The ratio of plasticizer to binder of 1.5 to 1.0 can be increased up to 4.0 to 1.0 with a further increase in energy gain.

While the present invention has been described by reference to particular embodiments thereof, it should be understood by those skilled in the art that all the modifications that are encompassed within the scope of the appended claims are intended to be included herein.

What is claimed is:

1. The compound, azidomethyl bis(fluorodinitroethyl) amine.

2. The compound, 0-(1,2-diazidopropyl)N,N-bis(-fluorodinitroethyl) amino methanol.

* * * * *